United States Patent
Ueda et al.

(10) Patent No.: US 10,512,532 B2
(45) Date of Patent: Dec. 24, 2019

(54) THERAPEUTIC DEVICE FOR THE TREATMENT METHODS AND INGUINAL HERNIA

(71) Applicant: Terumo Kabushiki Kaisha, Tokyo (JP)

(72) Inventors: Mariko Ueda, Fujinomiya (JP); Tatsuya Ouchi, Fujinomiya (JP); Toshiaki Shinohara, Fujinomiya (JP); Soichiro Sugihara, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 105 days.

(21) Appl. No.: 15/424,256

(22) Filed: Feb. 3, 2017

(65) Prior Publication Data
US 2017/0231745 A1  Aug. 17, 2017

(30) Foreign Application Priority Data
Feb. 16, 2016 (JP) .................... 2016-027178

(51) Int. Cl.
*A61F 2/04* (2013.01)
*A61F 2/00* (2006.01)

(52) U.S. Cl.
CPC .............. *A61F 2/04* (2013.01); *A61F 2/0063* (2013.01); *A61F 2002/0068* (2013.01); *A61F 2002/0072* (2013.01); *A61F 2002/045* (2013.01); *A61F 2210/0085* (2013.01)

(58) Field of Classification Search
CPC .................................................. A61M 29/00
USPC ........... 623/1.22–1.23, 23.69–23.7; 606/200; 600/37
See application file for complete search history.

(56) References Cited

U.S. PATENT DOCUMENTS

| | | | | |
|---|---|---|---|---|
| 2003/0130683 | A1* | 7/2003 | Andreas | A61F 2/88 606/200 |
| 2004/0236186 | A1* | 11/2004 | Chu | A61B 1/32 600/215 |
| 2010/0010631 | A1* | 1/2010 | Otte | A61F 2/0036 623/13.11 |

FOREIGN PATENT DOCUMENTS

WO  WO 2013/048272  4/2013

* cited by examiner

*Primary Examiner* — Yashita Sharma
(74) *Attorney, Agent, or Firm* — Jason H. Vick; Sheridan Ross, PC

(57) ABSTRACT

Provided is a method of treating inguinal hernia, in which a burden applied to a patient during treatment can be reduced. There is provided a method of treating inguinal hernia, in which a bowel is prevented from being exposed to an outside through a fascia. The method of treating inguinal hernia includes an introduction step of introducing a member configuring a structural body which restricts deformation of the bowel, through an anus toward a hernial site by using a transportation member; and a configuration step of configuring the structural body with respect to the bowel which stays medial to the fascia.

12 Claims, 11 Drawing Sheets

THERAPEUTIC DEVICE FOR THE TREATMENT METHODS AND INGUINAL HERNIA

CROSS REFERENCE TO RELATED APPLICATION

The present application claims the benefit of priority, under 35 U.S.C. § 119(e), to Japanese Patent Application No. 2016-027178, filed Feb. 16, 2016, entitled "Method of Treating Inguinal Hernia and Therapeutic Apparatus for Treating Inguinal Hernia," the entire disclosure of which is incorporated herein by reference, in its entirety, for all that it teaches and for all purposes.

TECHNICAL FIELD

The present disclosure relates to a method of treating inguinal hernia, in which the bowel is prevented from being exposed to the outside through the fascia, and a therapeutic apparatus for treating inguinal hernia.

BACKGROUND

Inguinal hernia is a disease in which a part of the bowel is exposed to the outside through a gap between the fascias. In a case where inguinal hernia is neglected and worsens, there are cases where the bowel is occluded, necrotized, or the like, thereby resulting in a critical state endangering a patient's life. Therefore, for example, a treatment may be performed in which a structural body (prosthesis) blocking a hernial site is caused to indwell in the hernial site of the patient and the bowel is prevented from being exposed to the outside through the fascia. For example, refer to the treatment described in Japanese Patent Application No. JP-T-2013-048272, the entire contents of which are hereby incorporated herein by reference for all that it teaches and for all purposes.

However, in a case where a hernial site of a patient is blocked by using a structural body, the body surface has to be incised along the shape of the structural body. Therefore, there is concern that invasiveness with respect to a human body increases and an excessive burden is applied to the patient.

SUMMARY

Technical Problem

The present disclosure addresses the aforementioned problem, and provides a method of treating inguinal hernia, in which a burden applied to the patient during treatment can be reduced, and a therapeutic apparatus for treating inguinal hernia.

Solution to Problem

A method of treating inguinal hernia is provided, in which a bowel is prevented from being exposed to an outside through a fascia. The method of treating inguinal hernia includes an introduction step of introducing a member configuring a structural body which restricts deformation of the bowel, through an anus toward a hernial site by using a transportation member; and a configuration step of configuring the structural body with respect to the bowel which stays medial to the fascia.

Advantageous Effect

According to the method of treating inguinal hernia, without incising a body surface of a patient, the structural body which restricts deformation of the bowel can be provided in the bowel of the patient through the anus in a minimally invasive manner. Therefore, a burden applied to the patient during treatment can be reduced by adopting the method of treating inguinal hernia.

DETAILED DESCRIPTION

Figure 1:
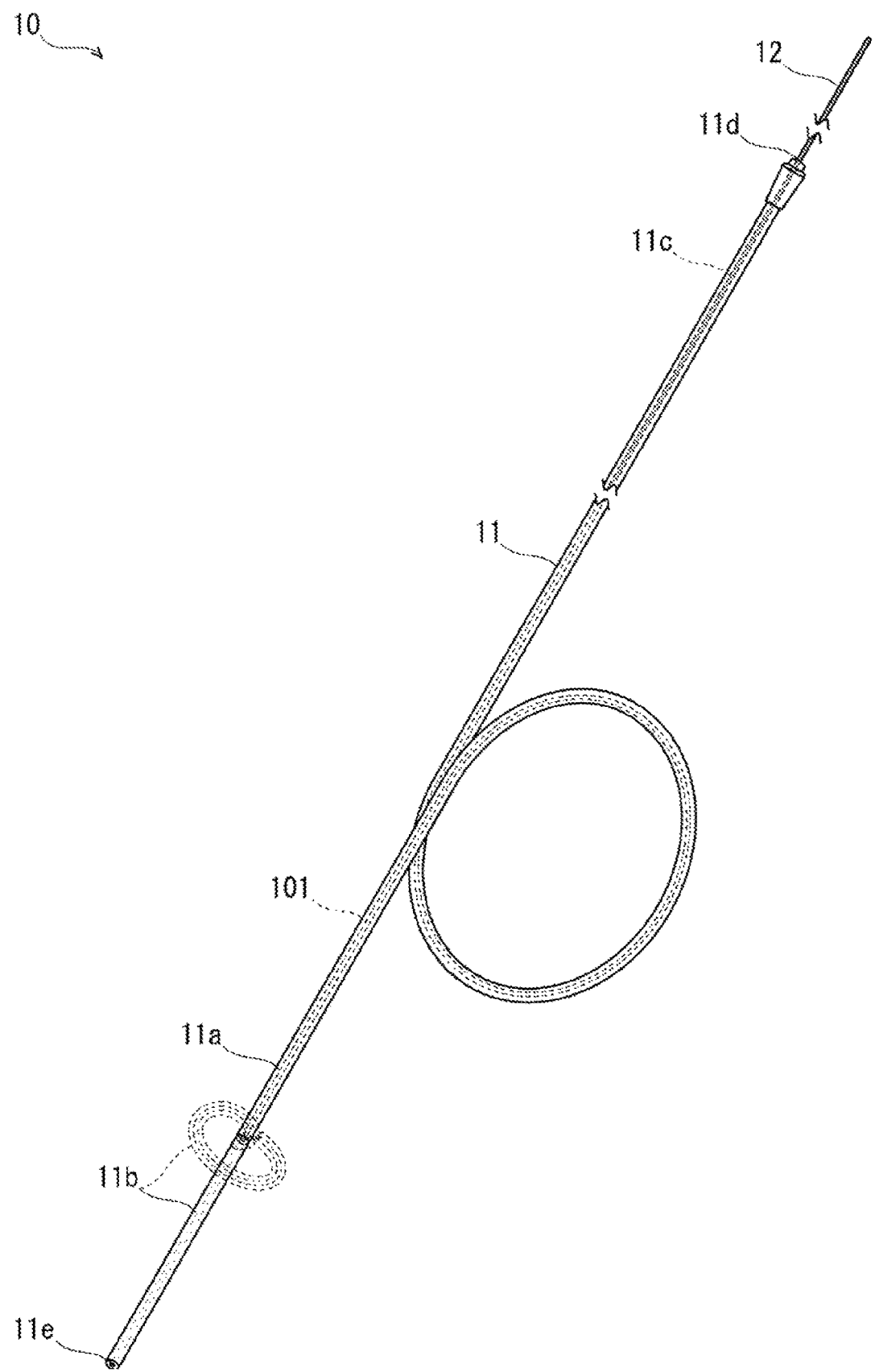
FIG. 1 is a perspective view illustrating an embodiment of a therapeutic apparatus.

Hereinafter, with reference to the accompanying drawings, embodiments of the present disclosure will be described. In the description of the drawings, the same reference signs will be applied to the same elements, and description thereof will be omitted without being repeated. For the convenience of description, there are cases where the sizes and the dimensional ratios of the members in the drawings are exaggerated and are different from the actual ratios. For example, in a therapeutic apparatus 10 an insertion portion 11d side of a catheter 11 may correspond to a proximal side, and a protruding portion 11e side of the catheter 11 may correspond to a distal side.

Embodiments of the therapeutic apparatus 10 and a stent 101 (structural body) used in a method of treating inguinal hernia will be described with reference to FIGS. 1, 2, and 4.

Figure 2:
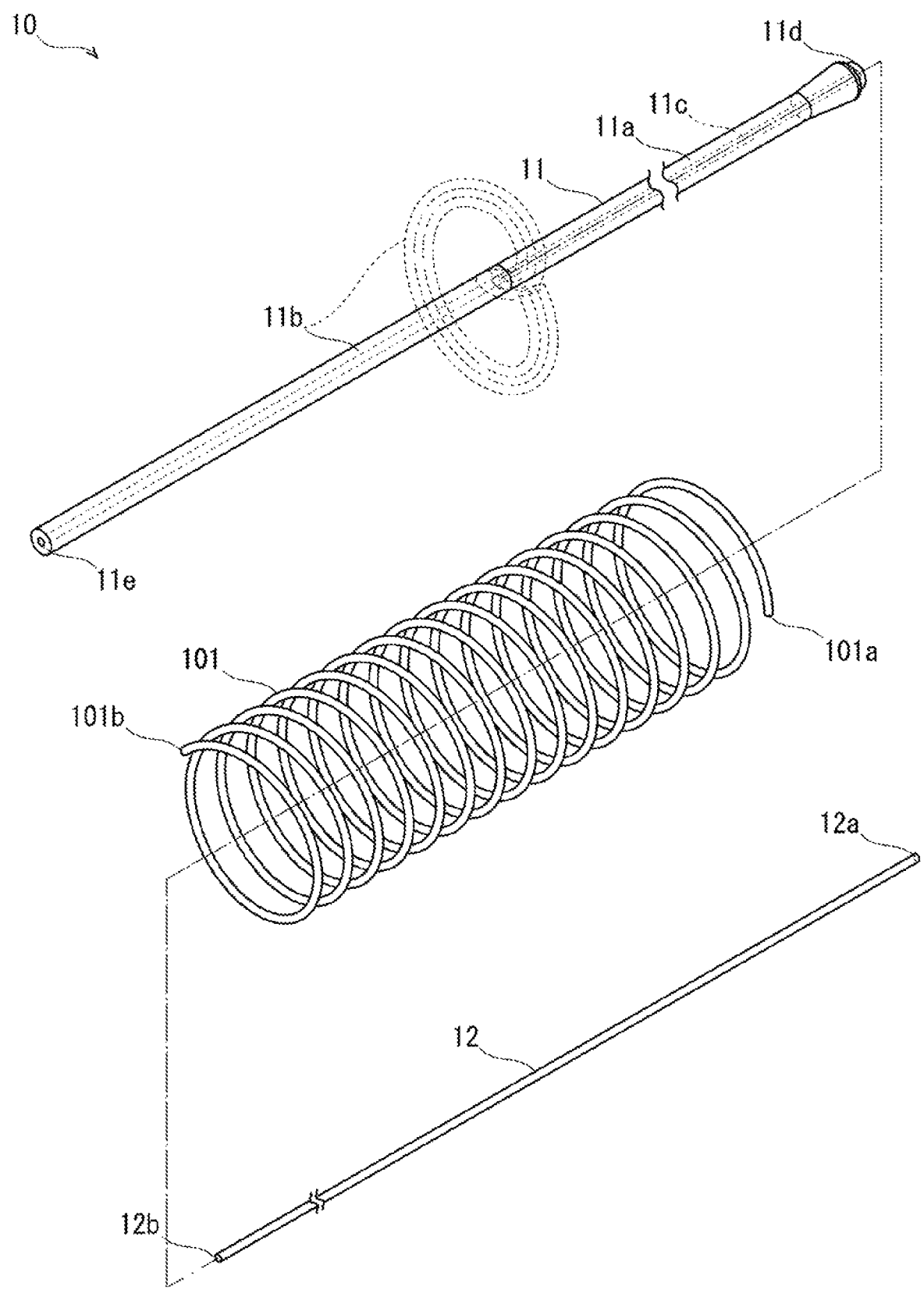
FIG. 2 is a perspective view illustrating the therapeutic apparatus of FIG. 1 and a stent.

FIG. 1 is a perspective view illustrating the therapeutic apparatus 10 in accordance with embodiments of the present disclosure. FIG. 2 is a perspective view illustrating a stent and the therapeutic apparatus 10 shown in FIG. 1.

The therapeutic apparatus 10 for treating inguinal hernia is a therapeutic apparatus for treating inguinal hernia, in which a bowel 502 is prevented from being exposed to the outside through a fascia 504.

The therapeutic apparatus 10 has a transportation member (catheter 11) that transports the stent 101 through an anus 501 toward a hernial site 503, and a push-out wire 12 that pushes out the stent 101 accommodated inside the catheter 11.

The catheter 11 is formed to have an elongated cylindrical shape. In the catheter 11, the linearly extending stent 101 inserted into a lumen 11c through the insertion portion 11d provided in a proximal portion 11a. In a portion of the proximal portion 11a, the catheter 11 holds the stent 101 in a linearly deformed state. A distal portion 11b of the catheter 11 is interlocked with the proximal portion 11a along an axial direction and is sufficiently short compared to the proximal portion 11a. In a portion of the distal portion 11b, when the stent 101 is restored to a spiral state, which is an original shape, the catheter 11 deforms to follow the shape of the stent 101. The catheter 11 guides the stent 101 inserted into the lumen 11c through the insertion portion 11d, to the outside through the protruding portion 11e via the proximal portion 11a and the distal portion 11b.

For example, the proximal portion 11a of the catheter 11 is configured to be made of a hard material having flexibility. The proximal portion 11a has hardness sufficient to maintain the stent 101 in a linear state and has softness capable of following the shape and movement of the bowel 502. For example, the distal portion 11b of the catheter 11 is configured to be made of a sufficiently soft material having flexibility. The distal portion 11b is deformed to follow resilience of the stent 101 and has softness capable of following the shape and movement of the bowel 502. A contrast marker for allowing a technician to perform visual recognition under the radioscopic conditions is provided in the proximal portion 11a of the catheter 11.

The push-out wire 12 is formed to have an elongated columnar shape. The outer diameter of the push-out wire 12 is slightly smaller than that of the lumen 11c of the catheter 11. When the technician grasps a proximal portion 12a side and operates the push-out wire 12, a distal portion 12b side is inserted into the lumen 11c through the insertion portion 11d of the catheter 11. The technician presses a proximal portion 101a of the stent 101 by using the distal portion 12b of the push-out wire 12, thereby pushing out the stent 101 to the protruding portion 11e side of the catheter 11. For example, the push-out wire 12 is configured to be made of a material similar to that of the proximal portion 11a of the stent 101.

In the description, the therapeutic apparatus 10 is configured to be used under the radioscopic conditions. However, the therapeutic apparatus 10 may be configured to be used in an endoscope (not illustrated).

The stent 101 is a member which restricts deformation of the bowel 502 and indwells along an inner wall of the bowel 502 at a site where hernia has occurred. The stent 101 may be formed by winding a slender and columnar member in a spiral state from the proximal portion 101a to a distal portion 101b and is configured to have a cylindrical shape corresponding to the inner wall of the bowel 502. The stent 101 is configured to be elastically deformable to return to the original spiral state after extending from the spiral state to a linear state. For example, the stent 101 is configured to be made of a shape memory alloy such as Ni—Ti (nickel-titanium). The stent 101 has softness capable of following the movement of the bowel 502. At least the outer circumferential surface of the stent 101 may be coated with a medicine for preventing synechia with respect to the bowel 502, and inflammation.

Here, the spiral stent 101 may be configured to be crimped in the catheter 11 and to be released by being unlocked. In other words, in a state where the stent 101 is locked by a claw and the claw is rotated by using an at-hand operation unit. The stent 101 may be configured to be increased in diameter and to be released when the stent 101 is unlocked by the claw.

Subsequently, with reference to FIGS. 3 to 6, description will be given regarding the method of treating inguinal hernia, in which the therapeutic apparatus 10 is adopted.

Figure 3:
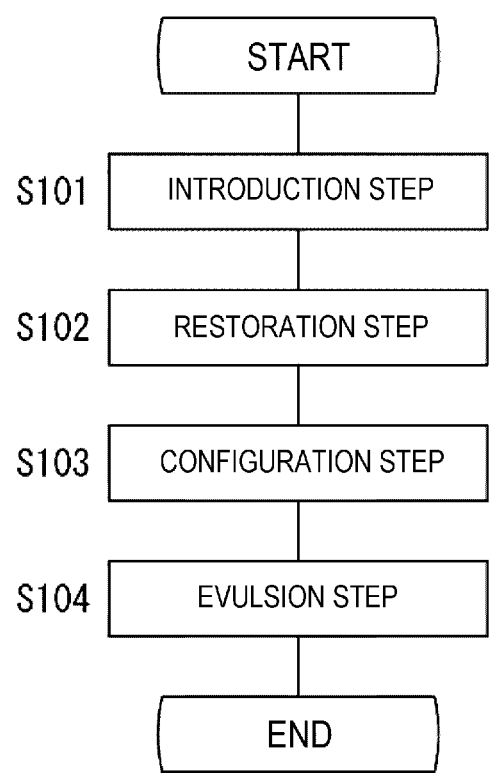
FIG. 3 is a flow chart illustrating an embodiment of a process of a method of treating inguinal hernia, in which the therapeutic apparatus is adopted.
Figure 5A:
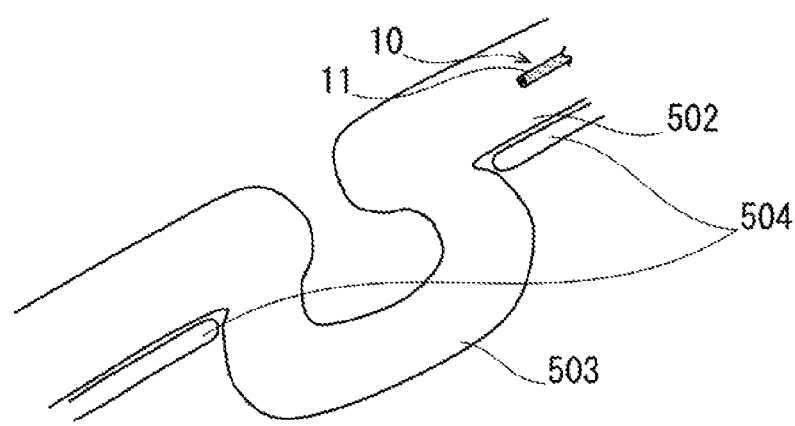
FIG. 5A is a close-up view illustrating the hernial site shown in FIG. 4 where the bowel of the patient is herniated out of the body through the fascia.
Figure 5B:
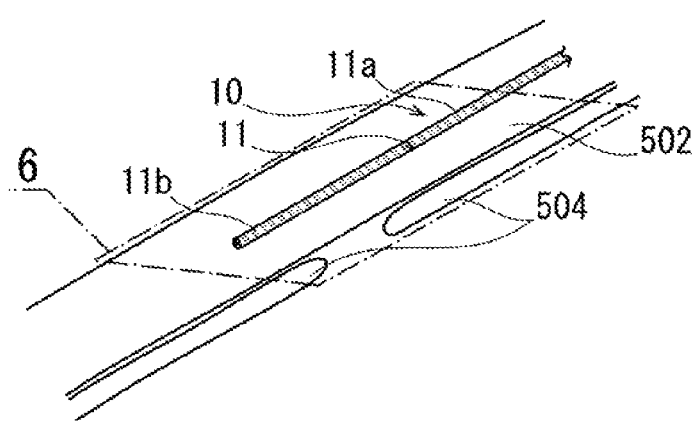
FIG. 5B is a view illustrating a state where after the bowel of the patient is caused to return to the inside of the body through the fascia, the distal portion of an embodiment of the therapeutic apparatus is inserted so as to reach the hernial site.
Figure 6A:
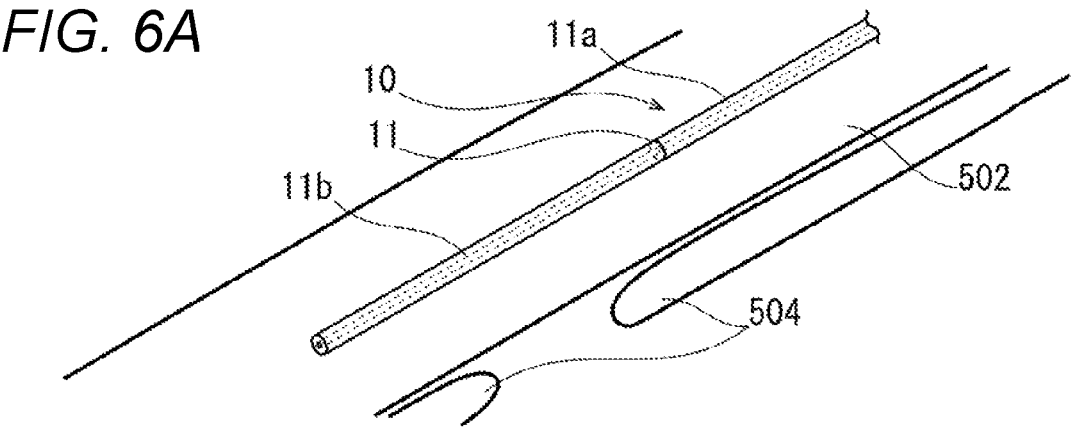
FIG. 6A is a close-up view of the hernia site and the embodiment of the therapeutic apparatus inserted as shown in FIG. 5B.
Figure 6B:
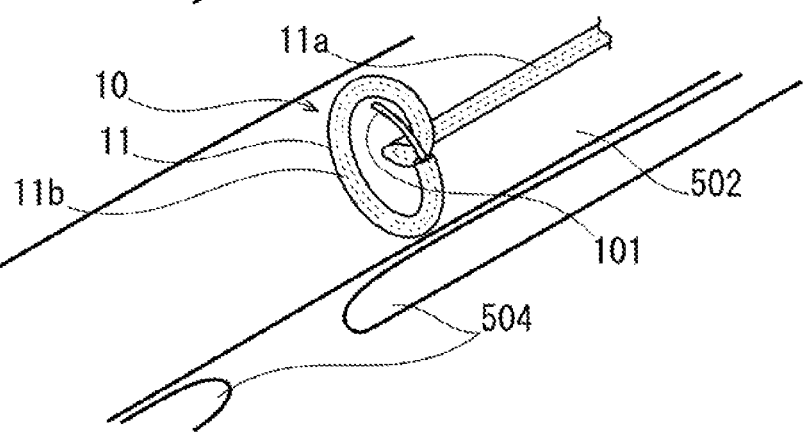
FIG. 6B is a view illustrating a state where a stent is pushed out through a proximal portion toward the distal portion of the therapeutic apparatus and the stent is slightly exposed inside the bowel in accordance with embodiments of the present disclosure.
Figure 6C:
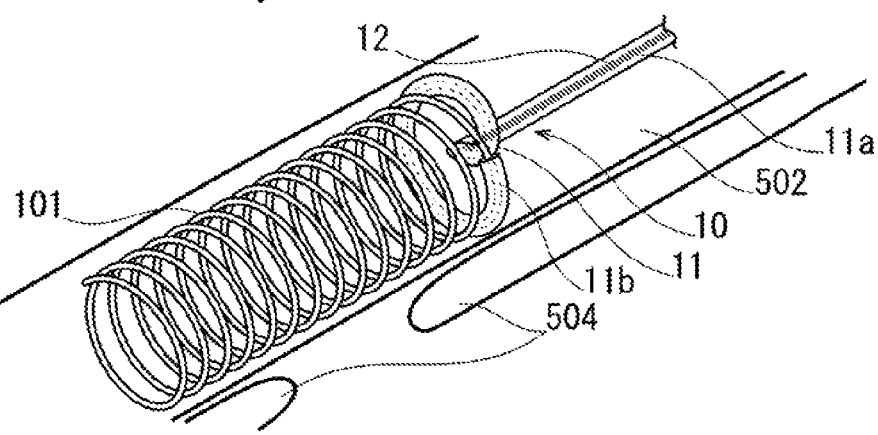
FIG. 6C is a view illustrating a state where the stent is pushed out through the distal portion of the therapeutic apparatus and indwells inside the bowel in accordance with embodiments of the present disclosure.
Figure 6D:
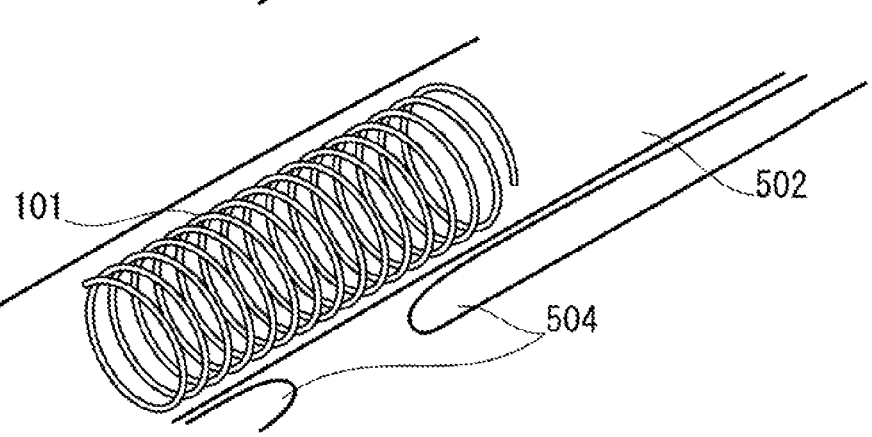
FIG. 6D is a view illustrating a state where the therapeutic apparatus is evulsed from the inside of the bowel in accordance with embodiments of the present disclosure.

FIG. 3 is a flow chart illustrating a process of the method of treating inguinal hernia, in which the therapeutic apparatus 10 is adopted. FIG. 4 is a view schematically illustrating the process of the method of treating inguinal hernia, in which the therapeutic apparatus 10 is adopted. The diagram illustrates a state where a distal portion of the therapeutic apparatus 10 is inserted through the anus 501 of a patient 500 to the vicinity of the hernial site 503. Being continued from the state of FIG. 4, FIG. 5A is a view illustrating the hernial site 503 where the bowel 502 of the patient 500 is herniated out of the body through the fascia 504, and FIG. 5B is a view illustrating a state where after the bowel 502 of the patient 500 is caused to return to the inside of the body through the fascia 504, the distal portion of the therapeutic apparatus 10 is inserted so as to reach a site which has been the hernial site 503. FIGS. 5A-5B schematically illustrates a region 5 shown in FIG. 4. Being continued from the state of FIGS. 5A-5B, FIG. 6A is a view corresponding to FIG. 5B, FIG. 6B is a view illustrating a state where the stent 101 is pushed out through a proximal portion toward the distal portion of the therapeutic apparatus 10 and the stent 101 is slightly exposed inside the bowel 502, FIG. 6C is a view illustrating a state where the stent 101 is pushed out through the distal portion of the therapeutic apparatus 10 and indwells inside the bowel 502, and FIG. 6D is a view illustrating a state where the therapeutic apparatus 10 is evulsed from the inside of the bowel 502. FIGS. 6A-6D schematically illustrates a region 6 shown in FIG. 5B.

An introduction step S101 (FIG. 3) is a step of introducing the stent 101 which restricts deformation of the bowel 502, through the anus 501 of the patient 500 toward the hernial site 503 by using the therapeutic apparatus 10. The introduction step S101 corresponds to the process illustrated in FIG. 4.

Figure 4:
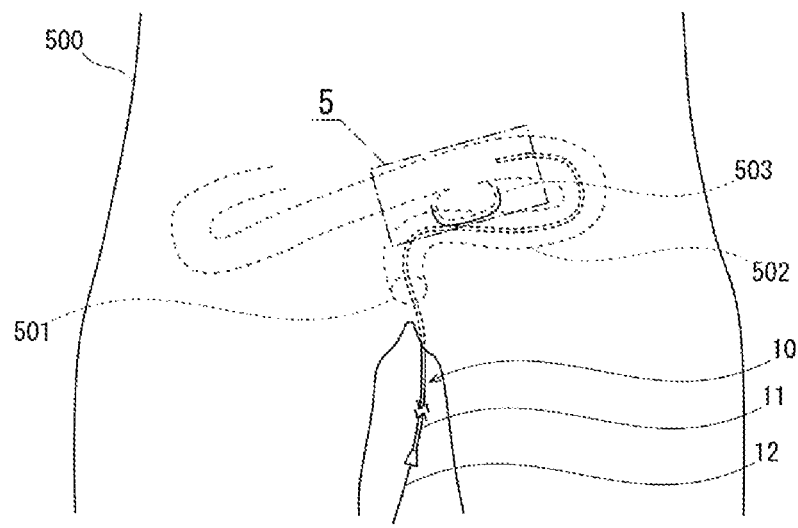
FIG. 4 is a view schematically illustrating an embodiment of the process of the method of treating inguinal hernia, in which the therapeutic apparatus is adopted.

As illustrated in FIG. 4, the technician (not illustrated, the same hereinafter) inserts the therapeutic apparatus 10 into the bowel 502 via the anus 501 of the patient 500 under the radioscopic conditions. The technician causes the distal portion 11b of the catheter 11 to be positioned in the vicinity of the hernial site 503.

A restoration step S102 (FIG. 3) is a step which is continued from the introduction step S101 and in which the hernial site 503 of the patient 500 is caused to return to a place medial to the fascia 504 by being pressed from the outside of the body. The restoration step S102 corresponds to the process illustrated in FIGS. 5A-5B.

As illustrated in FIGS. 5A and 5B, the technician presses the hernial site 503 from the body surface of the patient 500. Pressing force of the technician is transferred to the skin, the subcutaneous fat, and the peritoneum of the patient 500 in order. The hernial site 503 positioned under the peritoneum returns to the original position through a gap between the fascia 504 and the fascia 504 due to the pressing force of the technician.

The restoration step S102 is not necessary if the hernial site 503 of the patient 500 has returned to the original position medial to the fascia 504 during at least a surgical operation.

The restoration step S102 may be configured to be executed prior to the introduction step S101.

A configuration step S103 (FIG. 3) is a step which is continued from the restoration step S102 and in which the stent 101 is caused to indwell with respect to the bowel 502 which stays medial to the fascia 504. The configuration step S103 corresponds to the process illustrated in FIGS. 6A to 6C.

As illustrated in FIG. 6A, the technician causes the distal portion 11b of the catheter 11 to be positioned in the bowel 502 at the site where hernia has occurred (site which has returned to the normal position). As illustrated in FIG. 6B, the technician pushes out the stent 101 inserted into the proximal portion 11a of the catheter 11 to the distal portion 11b side of the catheter 11 by using the push-out wire 12. When the stent 101 is pushed out to the distal portion 11b beyond the proximal portion 11a of the catheter 11, the stent 101 is restored to the original spiral state. In other words, the distal portion 11b of the catheter 11 is elastically deformed to the spiral state along the shape of the stent 101. FIG. 6B illustrates a state where the stent 101 is pushed out to the distal portion 11b of the catheter 11 returns to the original spiral state and the stent 101 is slightly exposed through the distal portion 11b of the catheter 11. Moreover, as illustrated in FIGS. 6B and 6C, the technician further pushes out the stent 101 to the distal portion 11b side of the catheter 11 by using the push-out wire 12. As a result thereof, as illustrated in FIG. 6C, substantially the entirety of the stent 101 is pushed out through the proximal portion 11a of the catheter 11 and indwells inside the bowel 502.

Hernia of the bowel 502 may be configured to be prevented by continuously performing the restoration step S102 (pressing the bowel 502 performed by the technician from the body surface of the patient 500) while the configuration step S103 is executed.

An evulsion step S104 (FIG. 3) is a step which is continued from the configuration step S103 and in which the therapeutic apparatus 10 is evulsed from the bowel 502. The evulsion step S104 corresponds to the process illustrated in FIG. 6D.

As illustrated in FIG. 6D, the technician evulses the therapeutic apparatus 10 out of the body from the bowel 502 of the patient 500 via the anus 501 under the radioscopic conditions, thereby completing the surgical operation related to the inguinal hernia.

Hereinbefore, the method of treating inguinal hernia and the therapeutic apparatus 10 according to some embodiments exhibit operation effects through the below-described configuration.

According to the method of treating inguinal hernia, the bowel 502 is prevented from being exposed to the outside through the fascia 504. The method of treating inguinal hernia includes the introduction step S101 of introducing the member configuring the structural body which restricts deformation of the bowel 502, through the anus 501 toward the hernial site 503 by using the transportation member; and the configuration step S103 of configuring the structural body with respect to the bowel 502 which stays medial to the fascia 504.

According to the therapeutic apparatus 10 for treating inguinal hernia, the bowel 502 is prevented from being exposed to the outside through the fascia 504. The therapeutic apparatus 10 for treating inguinal hernia includes the transportation member that transports a member configuring a structural body which restricts deformation of the bowel 502, through the anus 501 toward the hernial site 503.

According to the method of treating inguinal hernia and the therapeutic apparatus 10, without incising the body surface of the patient 500, the structural body which restricts deformation of the bowel 502 can be provided in the bowel of the patient 500 through the anus in a minimally invasive manner. Therefore, a burden applied to the patient 500 during treatment can be reduced by adopting the method of treating inguinal hernia described herein.

Moreover, the treatment method has the restoration step S102 of causing the hernial site 503 to return to a place medial to the fascia 504 before the configuration step S103 by pressing the hernial site 503 from the outside of the body.

According to the method of treating inguinal hernia, even though the bowel 502 of the patient 500 is in a state of being exposed to the outside through the fascia 504, the structural body which restricts deformation of the bowel 502 can be provided in the bowel of the patient 500 through the anus in a minimally invasive manner without incising the body surface of the patient 500, after the hernial site 503 is caused to return to a place medial to the fascia 504. Therefore, even though the bowel 502 of the patient 500 is in a state of being exposed to the outside through the fascia 504, a burden applied to the patient 500 during treatment can be reduced by adopting the method of treating inguinal hernia as described herein.

Moreover, in the method of treating inguinal hernia, the member is the stent 101. In the configuration step S103, the stent 101 is caused to indwell with respect to the bowel 502 which stays medial to the fascia 504.

According to the method of treating inguinal hernia, hernia can be sufficiently prevented by applying the rigid stent 101 which has plentiful results and is highly versatile, as the member configuring the structural body which restricts deformation of the bowel 502. Therefore, a burden applied to the patient 500 during treatment can be sufficiently reduced and a relapse of hernia can be sufficiently prevented by adopting the method of treating inguinal hernia as described herein.

Moreover, in the method of treating inguinal hernia, in the introduction step S101, the stent 101 is introduced through the anus 501 toward the hernial site 503 in a state where the stent 101 is deformed from the spiral state to the linear state. In the configuration step S103, the stent 101 is caused to return to the original spiral state and to indwell with respect to the bowel 502.

According to the method of treating inguinal hernia, a load applied to the bowel 502 due to the stent 101 introduced through the anus 501 toward the hernial site 503 can be drastically reduced by drastically decreasing the stent 101 along a radial direction. Therefore, a burden applied to the patient 500 during treatment can be further reduced by adopting the method of treating inguinal hernia.

In some embodiments, the therapeutic apparatus 20 may include a structural body configured as an interlock ring 201, in place of the stent 101.

First, the configurations of the therapeutic apparatus 20 and the interlock ring 201 (structural body) adopted in the method of treating inguinal hernia will be described with reference to FIG. 7.

Figure 7A:
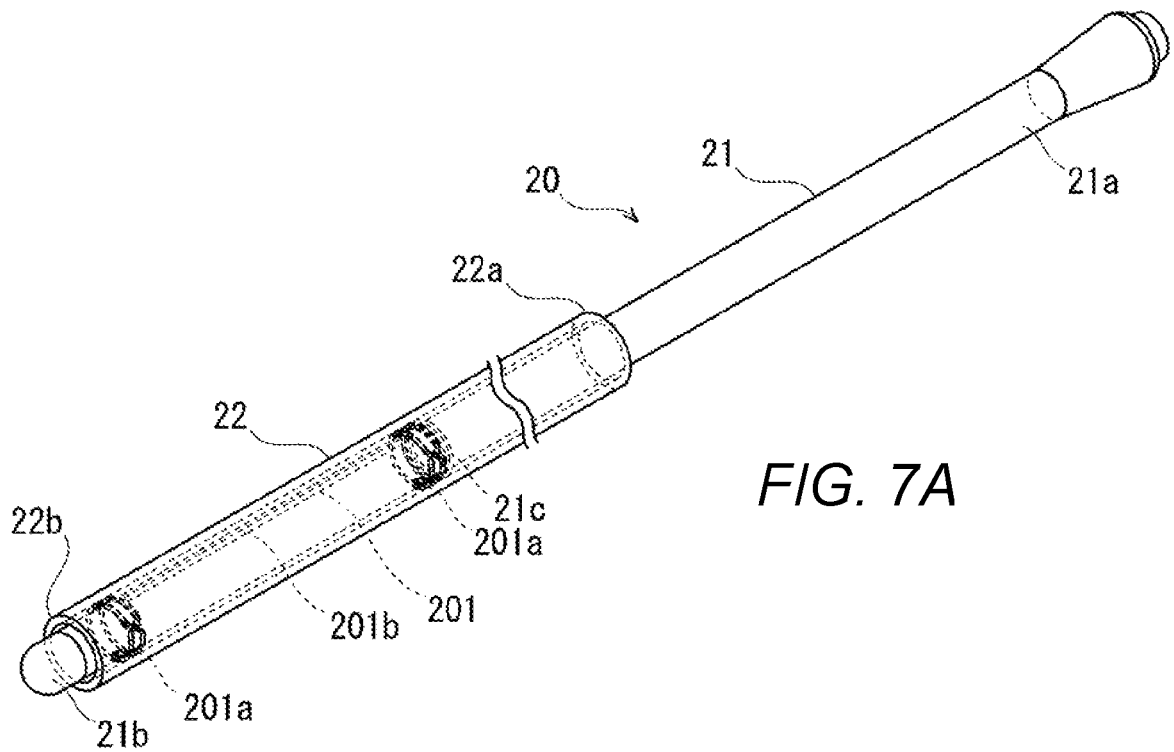
FIG. 7A is a perspective view illustrating an embodiment of a therapeutic apparatus having an interlock ring internally accommodated.
Figure 7B:
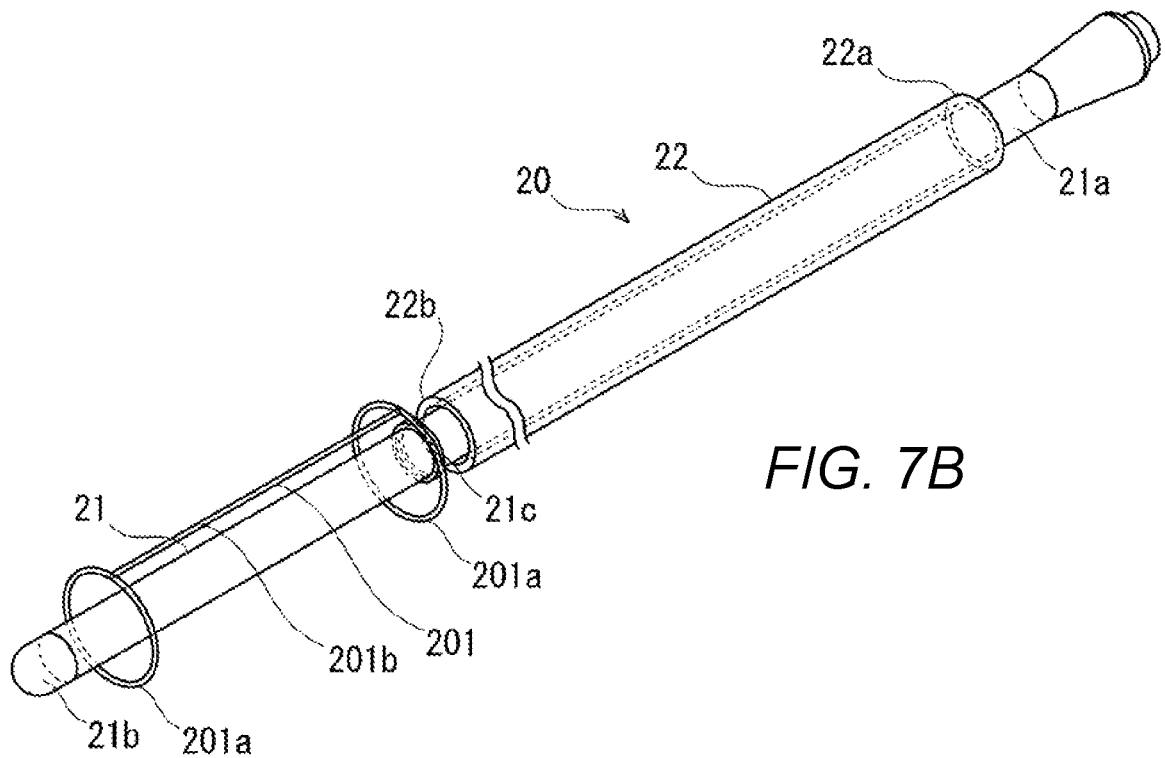
FIG. 7B is a perspective view illustrating an embodiment of the therapeutic apparatus and a state where an embodiment of the interlock ring is exposed to the outside.

FIGS. 7A and 7B are perspective views illustrating the therapeutic apparatus 20. FIG. 7A is a view illustrating a state where the interlock ring 201 is internally accommodated, and FIG. 7B is a view illustrating a state where the interlock ring 201 is exposed to the outside.

The therapeutic apparatus 20 has the transportation member (shaft 21) that transports the interlock ring 201 through the anus 501 toward the hernial site 503, and a cover sheath 22 that sandwiches and holds the interlock ring 201 together with the shaft 21.

The shaft 21 is configured to have an elongated columnar shape. The outer diameter of the shaft 21 is quite smaller than the inner diameter of an annular portion 201a of the interlock ring 201. A proximal portion 21a of the shaft 21 is grasped by the technician, and the interlock ring 201 is inserted through a portion of a distal portion 21b. A latch section 21c having an annular shape protruding radially outward is provided in a portion of the distal portion 21b in the shaft 21. The latch section 21c prevents the interlock ring 201 from moving to the proximal portion 21a side to follow the motion of the cover sheath 22. For example, the shaft 21 is configured to be made of a soft material having flexibility and has softness capable of following the shape and movement of the bowel 502. The contrast marker for allowing the technician to perform visual recognition under the radioscopic conditions is provided in a portion at the outermost distal end of the proximal portion 21a of the shaft 21.

The cover sheath 22 is formed to have an elongated cylindrical shape. The inner diameter of the cover sheath 22 is greater than the outer diameter of the shaft 21 by one size. The shaft 21 is inserted into the cover sheath 22. A proximal portion 22a of the cover sheath 22 is grasped by the technician, and a distal portion 22b holds the interlock ring 201 to cover the interlock ring 201. In this case, the annular portion 201a of the interlock ring 201 is bent in a figure-eight state along the outer shape of the shaft 21 and is decreased in diameter. For example, the cover sheath 22 is configured to be made of a soft material having flexibility and has softness capable of following the shape and movement of the bowel 502.

In the description, the therapeutic apparatus 20 is configured to be used under the radioscopic conditions. However, the therapeutic apparatus 20 may be configured to be used in an endoscope.

The interlock ring 201 is a member which restricts deformation of the bowel 502 and indwells along the inner wall of the bowel 502 at the site where hernia has occurred. The interlock ring 201 is formed by interlocking a pair of annularly-formed annular portions 201a with each other by a linearly-formed linear portion 201b and is configured to have a cylindrical shape corresponding to the inner wall of the bowel 502. In the interlock ring 201, at least a portion of the pair of annular portions 201a is configured to be elastically deformable to return to the original annular shape after being bent in a figure-eight shape and decreased in diameter, for example. For example, the interlock ring 201 is configured to be made of a shape memory alloy such as Ni—Ti (nickel-titanium). In the interlock ring 201, a portion of the linear portion 201b particularly has softness capable of following the movement of the bowel 502. At least the outer circumferential surface of the interlock ring 201 may be coated with a medicine for preventing synechia with respect to the bowel 502, and inflammation.

Subsequently, with reference to FIG. 8, description will be given regarding the method of treating inguinal hernia, in which the therapeutic apparatus 20 is adopted.

Figure 8A:
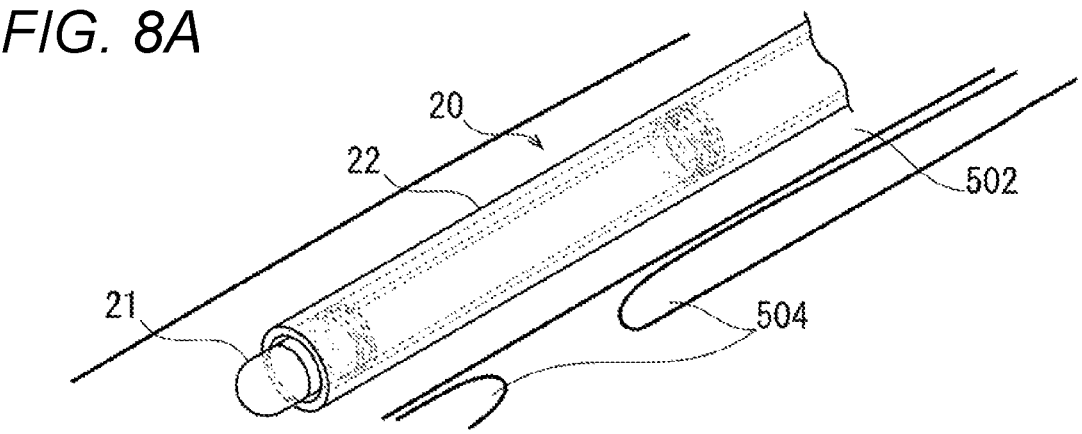
FIG. 8A is a view illustrating a state where the distal portion of the therapeutic apparatus is inserted into the bowel in accordance with embodiments of the present disclosure.
Figure 8B:
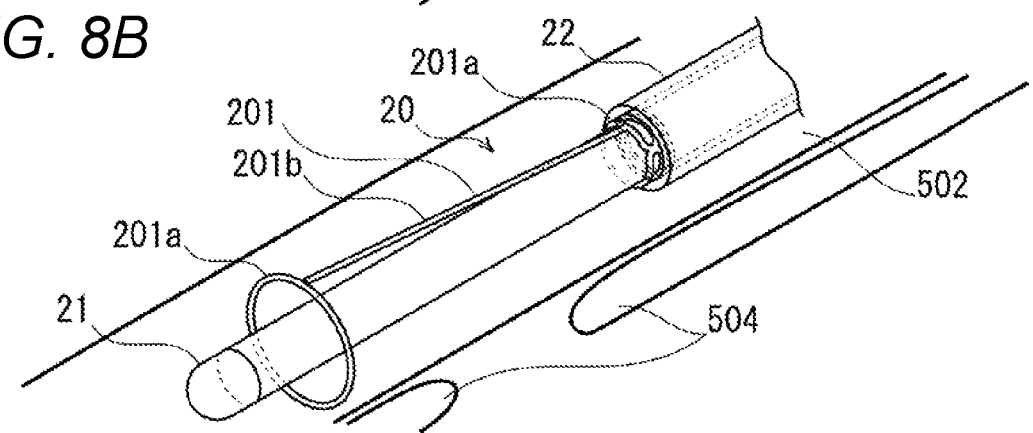
FIG. 8B is a view illustrating a state in the middle of exposing the interlock ring through the distal portion of the therapeutic apparatus inside the bowel in accordance with embodiments of the present disclosure.
Figure 8C:
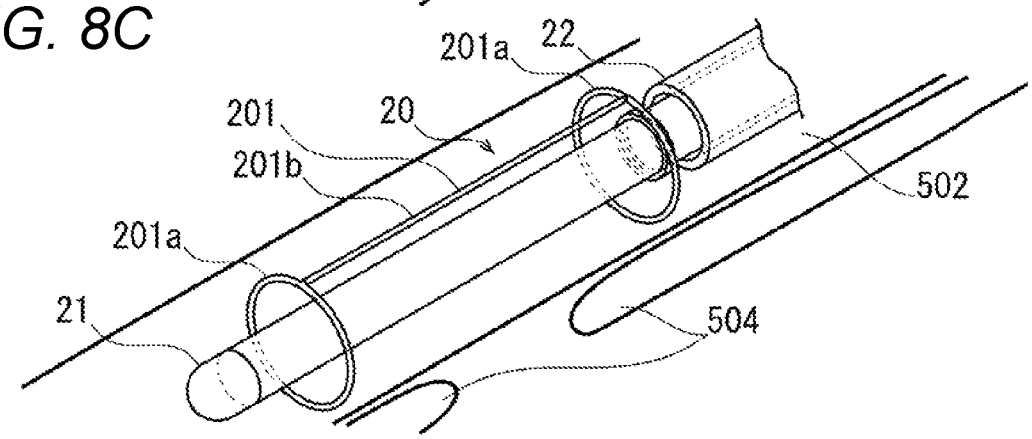
FIG. 8C is a view illustrating a state where the interlock ring is exposed through the distal portion of the therapeutic apparatus and indwells inside the bowel in accordance with embodiments of the present disclosure.
Figure 8D:
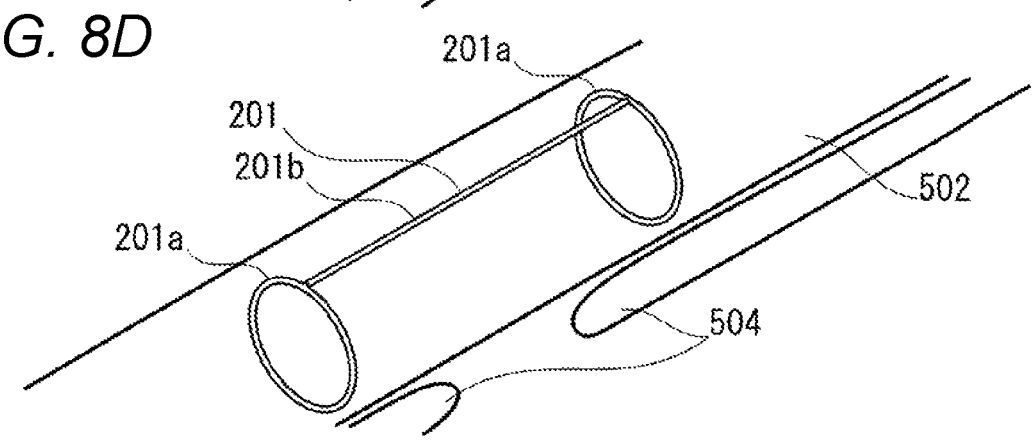
FIG. 8D is a view illustrating a state where the therapeutic apparatus is evulsed from the inside of the bowel in accordance with embodiments of the present disclosure.

FIGS. 8A-8D are perspective views schematically illustrating a main portion in the process of the method of treating inguinal hernia, in which the therapeutic apparatus 20 is adopted. FIG. 8A is a view illustrating a state where the distal portion of the therapeutic apparatus 20 is inserted into the bowel 502, FIG. 8B is a view illustrating a state in the middle of exposing the interlock ring 201 through the distal portion of the therapeutic apparatus 20 inside the bowel 502, FIG. 8C is a view illustrating a state where the interlock ring 201 is exposed through the distal portion of the therapeutic apparatus 20 and indwells inside the bowel 502, and FIG. 8D is a view illustrating a state where the therapeutic apparatus 20 is evulsed from the inside of the bowel 502.

The introduction step is a step of introducing the interlock ring 201 which restricts deformation of the bowel 502, through the anus 501 of the patient 500 toward the hernial site 503 by using the therapeutic apparatus 20. The introduction step corresponds to the process to the state immediately before that in FIG. 8A.

The technician inserts the therapeutic apparatus 20 into the bowel 502 via the anus 501 of the patient 500 under the radioscopic conditions. The technician causes the interlock ring 201 to be positioned in the vicinity of the hernial site 503.

The restoration step is similar to that previously described, and as such, description will be omitted. In addition, the restoration step may not be essential.

The configuration step is a step which is continued from the restoration step and in which the interlock ring 201 is caused to indwell with respect to the bowel 502 which stays medial to the fascia 504. The configuration step corresponds to the process illustrated in FIGS. 8A to 8C.

As illustrated in FIG. 8A, the technician causes the distal end (a portion accommodating the interlock ring 201) of the therapeutic apparatus 20 to be positioned in the bowel 502 at the site where hernia has occurred (site which has returned to a normal position). As illustrated in FIG. 8B, the technician pulls out the cover sheath 22 toward the proximal side of the shaft 21. In the interlock ring 201, the annular portion 201a exposed from the cover sheath 22 is restored to the original annular shape from the state of being bent in a figure-eight shape. FIG. 8B illustrates a state where the annular portion 201a on the distal side between the pair of annular portions 201a in the interlock ring 201 is released from the cover sheath 22 and returns to the original annular shape. Moreover, as illustrated in FIGS. 8B and 8C, the technician pulls out the cover sheath 22 from the shaft 21 toward the proximal side. As a result thereof, the annular portion 201a on the proximal side between the pair of annular portions 201a in the interlock ring 201 is also released from the cover sheath 22 and is restored to the original annular shape. As a result thereof, as illustrated in FIG. 8C, the interlock ring 201 is exposed from the cover sheath 22 of the therapeutic apparatus 20 and indwells inside the bowel 502.

The evulsion step is a step which is continued from the configuration step and in which the therapeutic apparatus 20 is evulsed from the bowel 502. The evulsion step corresponds to the process illustrated in FIG. 8D.

As illustrated in FIG. 8D, the technician evulses the therapeutic apparatus 20 out of the body from the bowel 502 of the patient 500 via the anus 501 under the radioscopic conditions.

In the method of treating inguinal hernia, in which the therapeutic apparatus 20 is adopted, the stent 101 may be configured to be used, in place of the interlock ring 201.

Hereinbefore, the method of treating inguinal hernia and the therapeutic apparatus 20 exhibit operation effects through the below-described configuration.

In the method of treating inguinal hernia, the member (interlock ring 201) is formed by interlocking the annularly-formed annular portions 201a by the linearly-formed linear portion 201b. In the configuration step, the interlock ring 201 is caused to indwell with respect to the bowel 502 which stays medial to the fascia 504.

According to the method of treating inguinal hernia, hernia can be sufficiently prevented by applying the simple and strong interlock ring 201 in which the annular portions 201a are interlocked with each other by the linear portion 201b, as the member configuring the structural body which restricts deformation of the bowel 502. Therefore, a burden applied to the patient 500 during treatment can be sufficiently reduced and a relapse of hernia can be sufficiently prevented by adopting the method of treating inguinal hernia.

In the method of treating inguinal hernia, in the introduction step, the annular portions 201a are introduced through the anus 501 toward the hernial site 503 in a state where the annular portions 201a are bent and decreased in diameter. In the configuration step, each of the annular portions 201a is caused to return to the original shape and the interlock ring 201 is caused to indwell with respect to the bowel 502.

According to the method of treating inguinal hernia, a load applied to the bowel 502 due to the interlock ring 201 introduced through the anus 501 toward the hernial site 503 can be reduced by decreasing the interlock ring 201 along the radial direction. Therefore, a burden applied to the patient 500 during treatment can be further reduced by adopting the method of treating inguinal hernia.

In some embodiments, the therapeutic apparatus 20 may use a structural body which is a short self-expandable-type stent 301 having interlock portions 301b at both ends thereof, in place of the stent 101.

First, the configurations of the therapeutic apparatus 20 and the stent 301 (structural body) adopted in the method of treating inguinal hernia will be described with reference to FIG. 9.

Figure 9A:
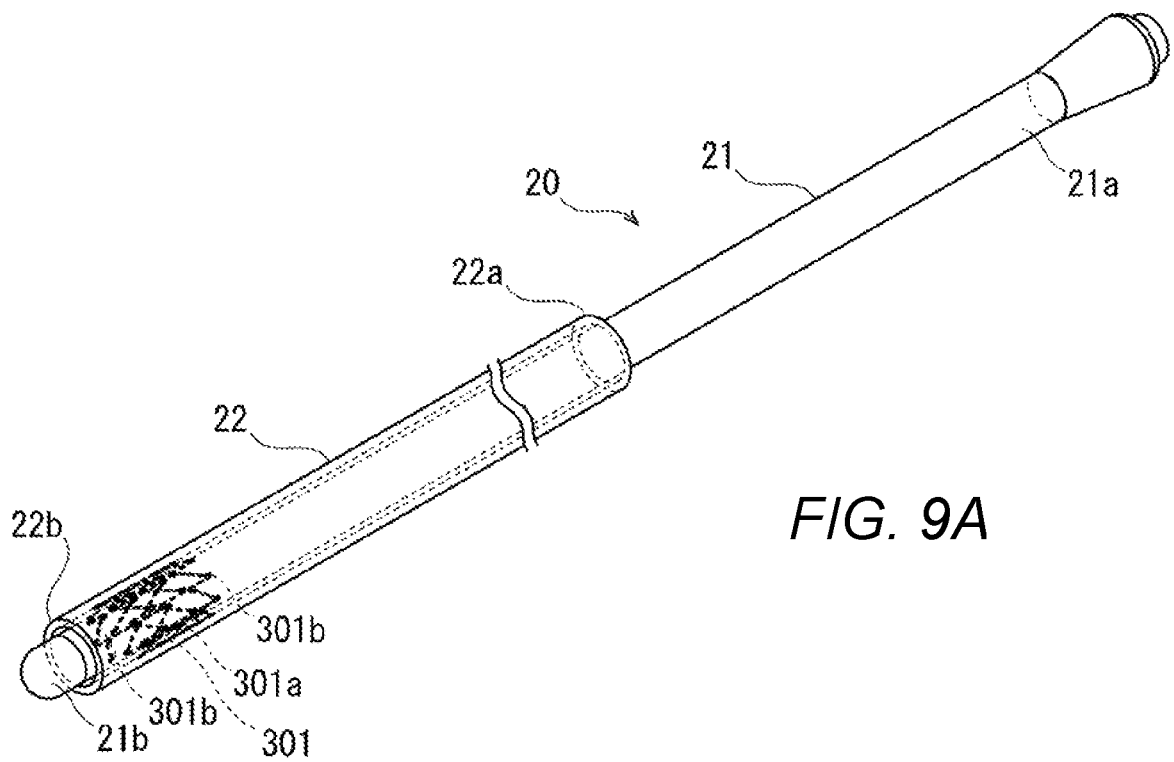
FIG. 9A is a view illustrating a state where an embodiment of the stent is internally accommodated in an embodiment of the therapeutic apparatus.
Figure 9B:
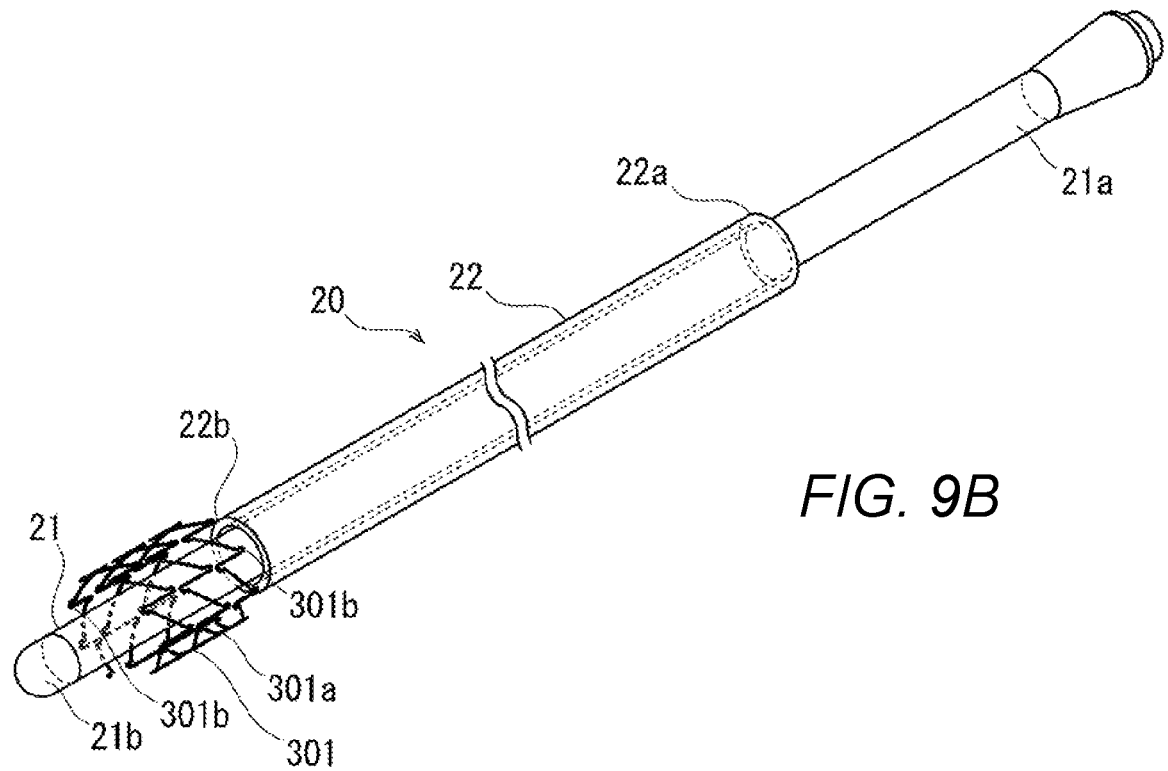
FIG. 9B is a view illustrating a state where the stent is exposed to the outside in accordance with embodiments of the present disclosure.

FIGS. 9A and 9B are perspective views illustrating the therapeutic apparatus 20 in accordance with embodiments of the present disclosure. FIG. 9A is a view illustrating a state where the stent 301 is internally accommodated, and FIG. 9B is a view illustrating a state where the stent 301 is exposed to the outside.

The stent 301 is a member which restricts deformation of the bowel 502 and indwells along the inner wall of the bowel 502 at the site where hernia has occurred. The stent 301 is a so-called self-expandable-type stent and has softness due to spiral portions 301a which are configured to be bent periodically and to be in a spiral state. In other words, the stent 301 has followability with respect to the deformation of the lumen. Particularly, the stent 301 has excellent deliverability due to the length along the axial direction formed to be shorter than that of a known stent.

For example, similar to the stent 101, the stent 301 is configured to be made by suitably selecting metal such as a known super-elastic alloy. At least the outer circumferential surface of the stent 301 may be coated with a medicine for preventing synechia with respect to the bowel 502, and inflammation.

In the stent 301, the interlock portions 301b respectively having polarities different from each other are bonded to both ends of the spiral portion 301a. Multiple interlock portions 301b are connected to protruding portions along the circumferential direction of the spiral portion 301a. The stent 301 is configured to be freely interlocked along the axial direction by the interlock portions 301b.

In the description, the therapeutic apparatus 20 is configured to be used under the radioscopic conditions. However, the therapeutic apparatus 20 may be configured to be used in an endoscope.

Subsequently, with reference to FIGS. 10A-10D, description will be given regarding the method of treating inguinal hernia, in which the therapeutic apparatus 20 is adopted.

Figure 10A:
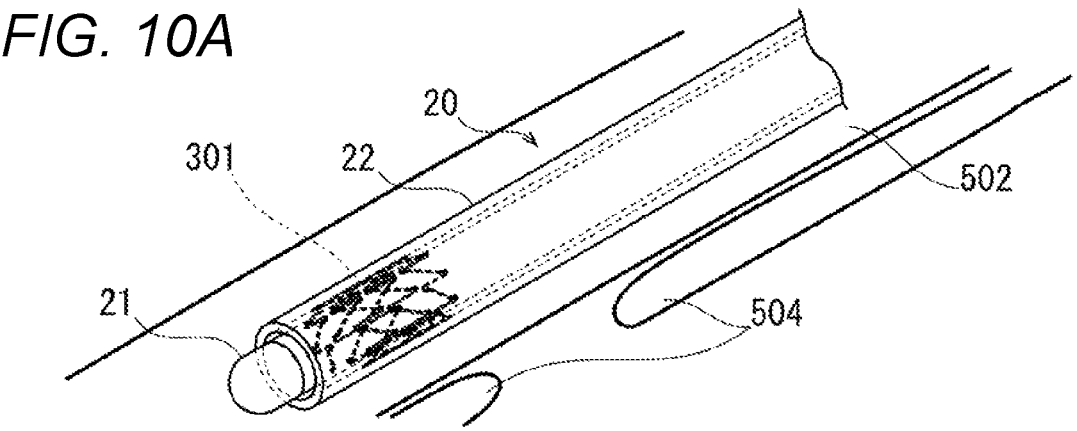
FIG. 10A is a view illustrating a state where the distal portion of an embodiment of the therapeutic apparatus is inserted into the bowel.
Figure 10B:
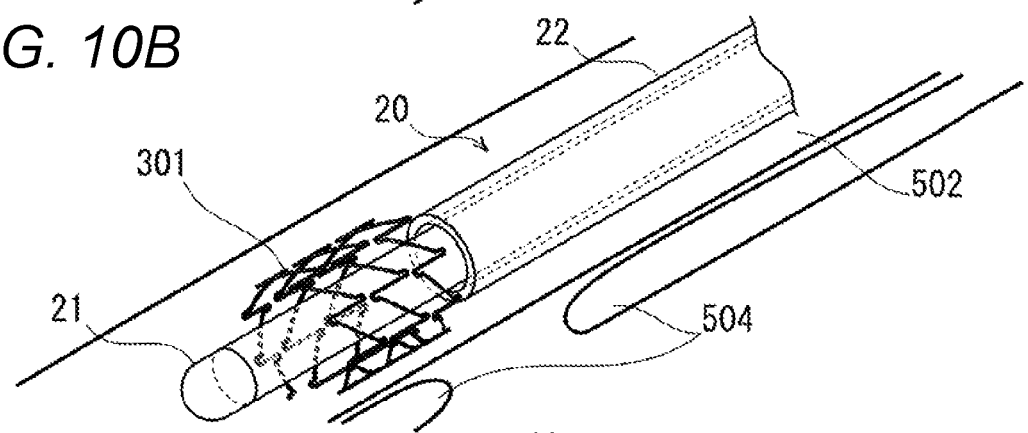
FIG. 10B is a view illustrating a state where the stent is exposed through the distal portion of the therapeutic apparatus and indwells inside the bowel in accordance with embodiments of the present disclosure.
Figure 10C:
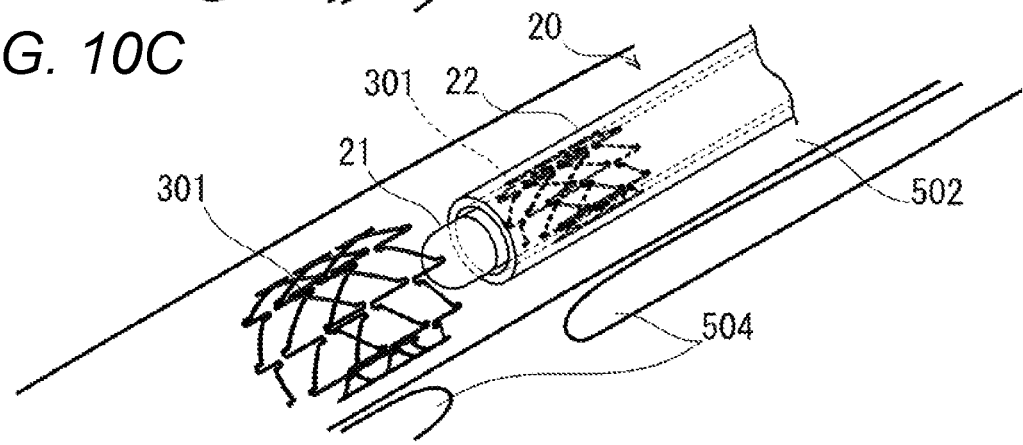
FIG. 10C is a view illustrating a state where the distal portion of the therapeutic apparatus accommodating a second stent approaches the stent which has indwelled inside the bowel in accordance with embodiments of the present disclosure.
Figure 10D:
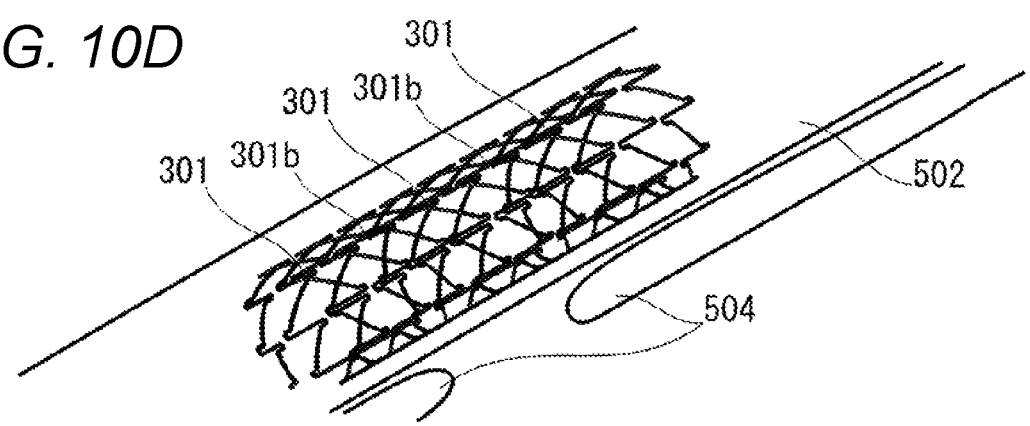
FIG. 10D is a view illustrating a state where a total of three stents are interlocked with each other and indwell inside the bowel in accordance with embodiments of the present disclosure.

FIG. 10A-10D are perspective views schematically illustrating a main portion in the process of the method of treating inguinal hernia, in which the therapeutic apparatus 20 is adopted. FIG. 10A is a view illustrating a state where the distal portion of the therapeutic apparatus 20 is inserted into the bowel 502, FIG. 10B is a view illustrating a state where the stent 301 is exposed through the distal portion of the therapeutic apparatus 20 and indwells inside the bowel 502, FIG. 10C is a view illustrating a state where the distal portion of the therapeutic apparatus 20 accommodating a second stent 301 approaches the stent 301 which has indwelled inside the bowel 502, and FIG. 10D is a view illustrating a state where a total of three stents 301 are interlocked with each other and indwell inside the bowel 502.

The introduction step is a step of introducing the stent 301 which restricts deformation of the bowel 502, through the anus 501 of the patient 500 toward the hernial site 503 by using the therapeutic apparatus 20. The introduction step corresponds to the process illustrated in FIG. 10A and the like.

The technician inserts the therapeutic apparatus 20 into the bowel 502 via the anus 501 of the patient 500 under the radioscopic conditions. The technician causes the stent 301 to be positioned in the vicinity of the hernial site 503. In other words, as illustrated in FIG. 10A, the technician causes the distal end (a portion accommodating the stent 301) of the therapeutic apparatus 20 to be positioned in the bowel 502 at the site where hernia has occurred (site which has returned to the normal position).

The restoration step is similar to that in the first embodiment, and description will be omitted. In addition, similar to the first embodiment, the restoration step is not essential.

The configuration step is a step which is continued from the restoration step and in which the stent 301 is caused to indwell with respect to the bowel 502 which stays medial to the fascia 504. The configuration step corresponds to the process illustrated in FIG. 10B and the like.

As illustrated in FIG. 10B, the technician pulls out the cover sheath 22 toward the proximal side of the shaft 21. As illustrated in FIG. 10C, the stent 301 is exposed from the cover sheath 22 and is restored to the original shape. As a result thereof, the stent 301 indwells inside the bowel 502. Here, the interlock portion 301b of the stent 301 which has already indwelled and the interlock portion 301b of the stent 301 which is indwelling are interlocked with each other by magnetic force. As illustrated in FIG. 10D, a total of three stents 301 are interlocked with each other.

The evulsion step is a step which is continued from the configuration step and in which the therapeutic apparatus 20 is evulsed from the bowel 502. The evulsion step corresponds to the process illustrated in FIG. 10D and the like.

As illustrated in FIG. 10D, every time the stent 301 is caused to indwell, the technician evulses the therapeutic apparatus 20 out of the body from the bowel 502 of the patient 500 via the anus 501 under the radioscopic conditions.

Hereinbefore, the method of treating inguinal hernia and the therapeutic apparatus 20 exhibit operation effects through the below-described configuration.

In the method of treating inguinal hernia, the member is the self-expandable-type stent 301. In the configuration step, the stent 301 is caused to indwell with respect to the bowel 502 which stays medial to the fascia 504.

According to the method of treating inguinal hernia, hernia can be sufficiently prevented by applying the rigid self-expandable-type stent 301 which has plentiful results and is highly versatile, as the member configuring the structural body which restricts deformation of the bowel 502. Therefore, a burden applied to the patient 500 during treatment can be sufficiently reduced and a relapse of hernia can be sufficiently prevented by adopting the described method of treating inguinal hernia.

In the method of treating inguinal hernia, the stent 301 includes the interlock portion 301b at the end portion along the axial direction. In the configuration step, the multiple stents 301 are interlocked with each other via the interlock portion 301b and are caused to indwell with respect to the bowel 502.

According to the method of treating inguinal hernia, even though the inside of the bowel 502 from the anus 501 to the hernial site 503 is curved, the stent 301 which is shortened in length along the axial direction by being dividedly configured can be smoothly inserted into the bowel 502. In other words, a load applied to the bowel 502 due to introduction of the stent can be drastically reduced by adopting the stent 301 which is divided, is shortened in length, and has excellent deliverability. Therefore, a burden applied to the patient 500 during treatment can be further reduced by adopting the method of treating inguinal hernia as described herein.

A therapeutic apparatus 40 may use a structural body which is formed by curing a photo-curable resin 401, in place of the stent 101.

First, the configurations of the therapeutic apparatus 40 and the to-be-cured photo-curable resin 401 (structural body) adopted in the method of treating inguinal hernia will be described with reference to FIG. 11.

Figure 11:
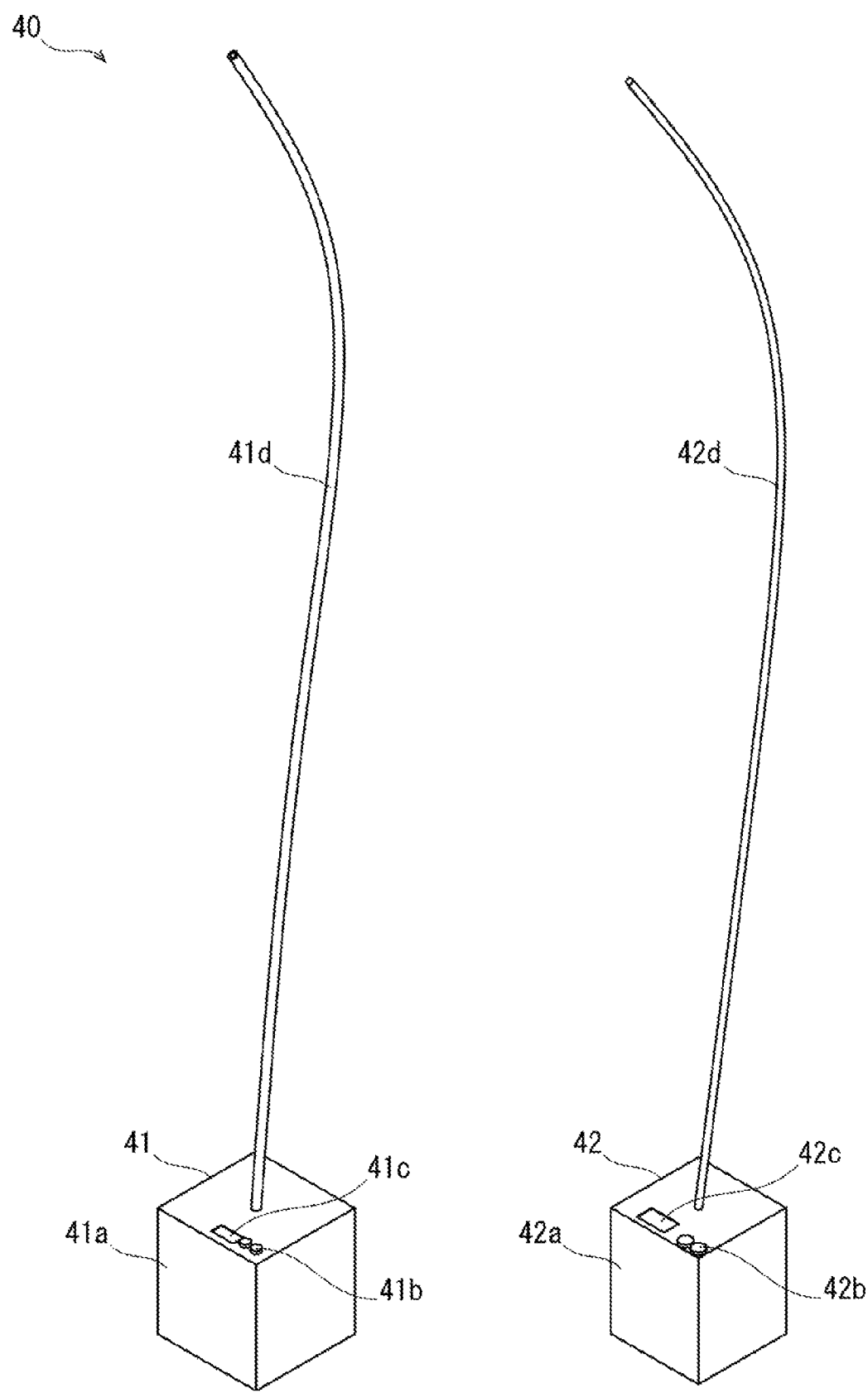
FIG. 11 is a perspective view illustrating an embodiment of a therapeutic apparatus.

FIG. 11 is a perspective view illustrating the therapeutic apparatus 40 in accordance with embodiments of the present disclosure.

The therapeutic apparatus 40 has a transportation member (sprayer 41) that transports the photo-curable resin 401 through the anus 501 toward the hernial site 503, and an ultraviolet-ray irradiator 42 that cures the photo-curable resin 401 sprayed onto the inner wall of the bowel 502.

As the sprayer 41, a known sprayer is used. The liquefied photo-curable resin 401 stored in a main body portion 41a is sprayed via an elongated liquid feeding hose 41d which is interlocked with the main body portion 41a. A contrast marker for allowing the technician to perform visual recognition under the radioscopic conditions is provided in a portion at the outermost distal end of the liquid feeding hose 41d. The spraying amount and the spraying pressure of the photo-curable resin 401 are set with a switch 41b provided in the main body portion 41a, and the set values are checked through a display 41c. The switch 41b may be configured to be a foot pedal-type switch.

As the ultraviolet-ray irradiator 42, a known device is used. Light emitted from a light source provided in a main body portion 42a is guided out via an optical fiber 42d which is interlocked with the main body portion 42a. A contrast marker for allowing the technician to perform visual recognition under the radioscopic conditions is provided in a portion at the outermost distal end of the optical fiber 42d. The intensity of an ultraviolet ray is set with a switch 42b provided in the main body portion 42a, and the set value is checked through a display 42c. The switch 42b may be configured to be a foot pedal-type switch.

In the description, the therapeutic apparatus 40 is configured to be used under the radioscopic conditions. However, the therapeutic apparatus 40 may be configured to be used in an endoscope.

The therapeutic apparatus 40 may be configured to have the liquid feeding hose 41d of the sprayer 41 and the optical fiber 42d of the ultraviolet-ray irradiator 42 in a coaxially bundled manner.

The photo-curable resin 401 is cured and serves as the member configuring the structural body which restricts deformation of the bowel 502. When the photo-curable resin 401 is irradiated with an ultraviolet ray after being sprayed along the inner wall of the bowel 502 at the site where hernia has occurred, the photo-curable resin 401 is cured. For example, the photo-curable resin 401 is configured to be made of a liquefied epoxy resin. When the photo-curable resin 401 is configured to be made of a material which is unlikely to transmit an X-ray, the technician can easily check the spraying state under the radioscopic conditions with respect to the inner wall of the bowel 502.

Subsequently, with reference to FIGS. 12A-12D, description will be given regarding the method of treating inguinal hernia, in which the therapeutic apparatus 40 is adopted.

Figure 12A:
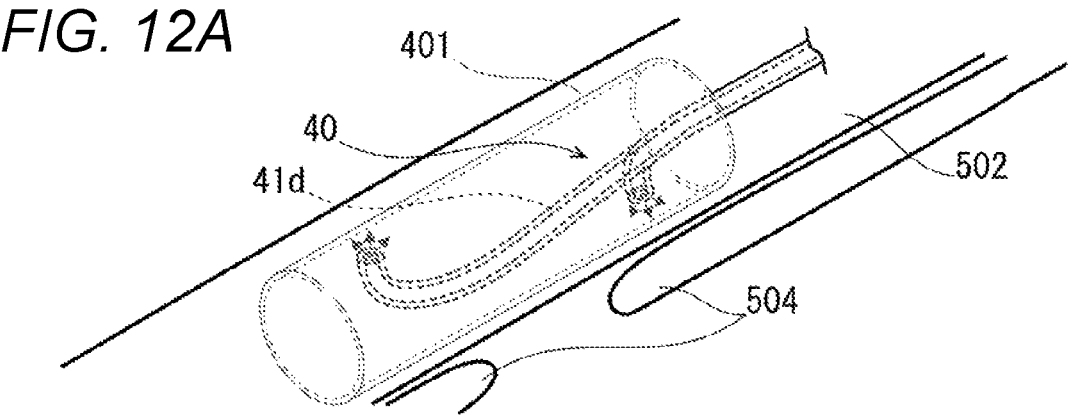
FIG. 12A is a view illustrating a state where the inside of the bowel is coated with a photo-curable resin which is sprayed by using a sprayer in accordance with embodiments of the present disclosure.
Figure 12B:
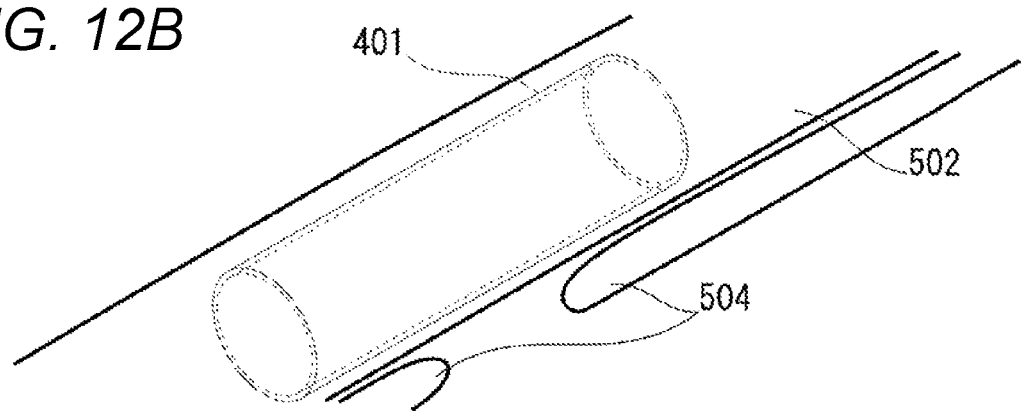
FIG. 12B is a view illustrating a state where the sprayer is evulsed from the inside of the bowel in accordance with embodiments of the present disclosure.
Figure 12C:
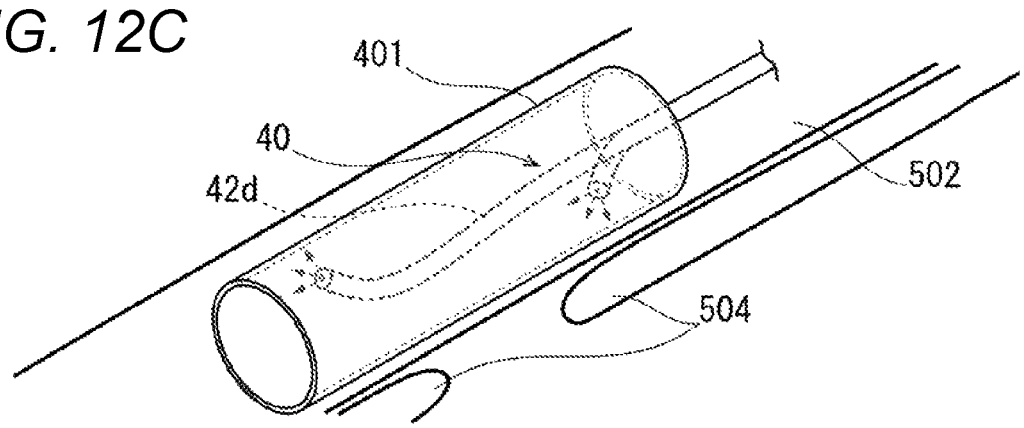
FIG. 12C is a view illustrating a state where the photo-curable resin inside the bowel is cured by using an ultraviolet-ray irradiator in accordance with embodiments of the present disclosure.
Figure 12D:
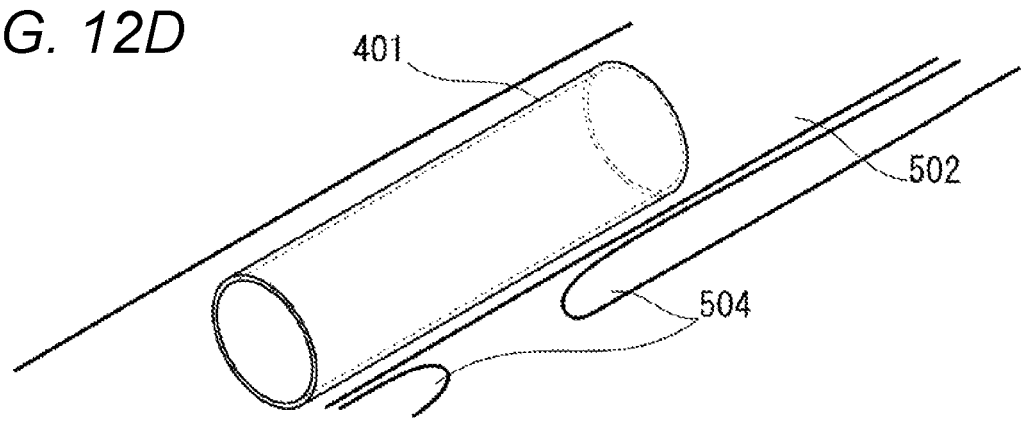
FIG. 12D is a view illustrating a state where the ultraviolet-ray irradiator is evulsed from the inside of the bowel in accordance with embodiments of the present disclosure.

FIGS. 12A-12D are perspective views schematically illustrating a main portion in the process of the method of treating inguinal hernia, in which the therapeutic apparatus 40 is adopted. FIG. 12A is a view illustrating a state where the inside of the bowel 502 is coated with the photo-curable resin 401 which is sprayed by using the sprayer 41, FIG. 12B is a view illustrating a state where the sprayer 41 is evulsed from the inside of the bowel 502, FIG. 12C is a view illustrating a state where the photo-curable resin 401 inside the bowel 502 is cured by using the ultraviolet-ray irradiator 42, and FIG. 12D is a view illustrating a state where the ultraviolet-ray irradiator 42 is evulsed from the inside of the bowel 502.

The introduction step is a step of introducing the photo-curable resin 401 which restricts deformation of the bowel 502 while being in a cured state, through the anus 501 of the patient 500 toward the hernial site 503 by using the sprayer 41 which is the therapeutic apparatus 40. The introduction step corresponds to the process illustrated in FIG. 12A. As illustrated in FIG. 12A, the technician inserts the liquid feeding hose 41d of the sprayer 41 which is the therapeutic apparatus 40 into the bowel 502 via the anus 501 of the patient 500 under the radioscopic conditions. The technician causes the distal end of the liquid feeding hose 41d of the sprayer 41 to be positioned in the vicinity of the hernial site 503.

The restoration step is similar to that in the first embodiment, and description will be omitted. In addition, similar to the first embodiment, the restoration step is not essential.

The configuration step is a step which is continued from the restoration step and in which the bowel 502 which stays medial to the fascia 504 is coated with the photo-curable resin 401.

The configuration step corresponds to the process illustrated in FIG. 12A. As illustrated in FIG. 12A, while moving the liquid feeding hose 41d of the sprayer 41 along the axial direction and the radial direction inside the bowel 502, the technician sprays the photo-curable resin 401 onto the inner wall of the bowel 502 in a cylindrical shape. Thereafter, in the evulsion step, as illustrated in FIG. 12B, the technician evulses the liquid feeding hose 41d of the sprayer 41 out of the body from the bowel 502 of the patient 500 via the anus 501 under the radioscopic conditions.

Moreover, the introduction step is a step of causing the optical fiber 42d of the ultraviolet-ray irradiator 42 to face the photo-curable resin 401 sprayed onto the inner wall of the bowel 502. The introduction step also corresponds to the process illustrated in FIG. 12C. As illustrated in FIG. 12C, the technician inserts the optical fiber 42d of the ultraviolet-ray irradiator 42 which is the therapeutic apparatus 40 into the bowel 502 via the anus 501 of the patient 500 under the radioscopic conditions, and the technician causes the optical fiber 42d to face the photo-curable resin 401 sprayed onto the inner wall of the bowel 502.

Moreover, the configuration step is a step of curing the photo-curable resin 401 sprayed onto the inner wall of the bowel 502 by irradiating the photo-curable resin 401 with an ultraviolet ray. The configuration step also corresponds to the process illustrated in FIG. 12C. As illustrated in FIG. 12C, while moving the optical fiber 42d of the ultraviolet-ray irradiator 42 along the axial direction and the radial direction inside the bowel 502, the technician cures the photo-curable resin 401 sprayed onto the inner wall of the bowel 502 by irradiating the photo-curable resin 401 with an ultraviolet ray. Thereafter, in the evulsion step, as illustrated in FIG. 12D, the technician evulses the optical fiber 42d of the ultraviolet-ray irradiator 42 from the bowel 502 of the patient 500 via the anus 501 under the radioscopic conditions.

Hereinbefore, the method of treating inguinal hernia and the therapeutic apparatus 40 exhibit operation effects through the below-described configuration.

In the method of treating inguinal hernia, the member (photo-curable resin 401) is made of a resin which is cured by being irradiated with light. In the introduction step, the bowel 502 which stays medial to the fascia 504 is coated with the photo-curable resin 401. In the configuration step, the photo-curable resin 401 is cured by being irradiated with light.

According to the method of treating inguinal hernia, the structural body can be configured to individually match the shape of the bowel 502 of the patient 500. In other words, the structural body formed by curing the photo-curable resin 401 can be individually configured along the shape of the inner wall of the bowel 502 of the patient 500. Moreover, according to the method of treating inguinal hernia, the strength of the structural body formed by curing the photo-curable resin 401 can be arbitrarily set depending on the thickness of the resin layer coating the bowel 502, or the specification. Moreover, according to the method of treating inguinal hernia, since the photo-curable resin 401 to be introduced through the anus 501 toward the hernial site 503 is in a state before being cured and does not have a fixed form, a load applied to the bowel 502 during the introduction can be reduced. Therefore, a burden applied to the patient 500 during treatment can be sufficiently reduced and a relapse of hernia can be sufficiently prevented by adopting the method of treating inguinal hernia as described herein.

Hereinbefore, favorable embodiments of the present disclosure have been described. However, the embodiments are exemplifications for describing the present disclosure, and the scope of the present disclosure is not intended to be limited to only the embodiments described. Therefore, the present disclosure can be executed in various forms different from those in the above-described embodiments without departing from the gist thereof. In other words, the present disclosure can be variously modified and changed based on the configurations disclosed in Claims, and the modifications and changes are also included in the scope of the present disclosure.

REFERENCE SIGNS LIST 10, 20, 30, 40 THERAPEUTIC APPARATUS,
11 CATHETER,

12 PUSH-OUT WIRE,
21 SHAFT,
22 COVER SHEATH,
31 HOLDING PORTION,
32 GUIDE PORTION,
41 SPRAYER,
42 ULTRAVIOLET-RAY IRRADIATOR,
101 STENT,
201 INTERLOCK RING,
201a ANNULAR PORTION,
201b LINEAR PORTION,
301 STENT,
301b INTERLOCK PORTION,
401 PHOTO-CURABLE RESIN,
501 ANUS,
502 BOWEL,
503 HERNIAL SITE,
S101 INTRODUCTION STEP,
S102 RESTORATION STEP,
S103 CONFIGURATION STEP, AND
S104 EVULSION STEP.

What is claimed is:

1. A method of treating inguinal hernia, in which a bowel is prevented from being exposed to an outside of a body of a patient through a fascia at a hernial site, the method comprising:
   an introduction step of introducing, without incising the body of the patient, a member comprising a structural body which restricts deformation of the bowel, through an anus and in a direction toward the hernial site by using a transportation member that transports the structural body;
   a configuration step of positioning the structural body with respect to the hernial site inside the bowel and deploying the structural body from the transportation member, wherein the structural body is pushed out of the transportation member and caused to indwell inside the bowel and remain in a position medial to the fascia; and
   an evulsion step of removing the transportation member from the body of the patient and bowel via the anus while the structural body remains in the position inside the bowel at the position medial to the fascia.

2. The method of treating inguinal hernia according to claim 1, further comprising:
   a restoration step of causing the hernial site to return to a place medial to the fascia before the configuration step by pressing the hernial site from the outside of the body of the patient.

3. The method of treating inguinal hernia according to claim 1,
   wherein the member is a stent, and
   wherein in the introduction step, the stent is held inside the transportation member.

4. The method of treating inguinal hernia according to claim 3,
   wherein in the introduction step, the stent is introduced through the anus and in the direction toward the hernial site in a state where the stent is deformed from an original spiral state to a deformed linear state, and
   wherein in the configuration step, the stent is caused to return to the original spiral state and to indwell with respect to the bowel in the original spiral state.

5. The method of treating inguinal hernia according to claim 1,
   wherein the member is a self-expandable-type stent, and
   wherein in the introduction step, the stent is held inside the transportation member in an elastically deformed state.

6. The method of treating inguinal hernia according to claim 1, wherein the introduction step, the configuration step, and the evulsion step are all completed without incising a surface of the body of the patient.

7. The method of treating inguinal hernia according to claim 1, wherein the stent is made from a shape memory alloy.

8. The method of treating inguinal hernia according to claim 1, wherein the structural body is coated with a medicine that prevents inflammation of the bowel and prevents adhesion of the structural body with the bowel.

9. The method of treating inguinal hernia according to claim 1, wherein in the configuration step the structural body is pushed out of the transportation member via a push wire disposed at least partially within a lumen of the transportation member and running from the structural member to a point outside of the body of the patient, and wherein the push wire is configured to move independently of the transportation member.

10. The method of treating inguinal hernia according to claim 1, wherein prior to the introduction step, the structural body is crimped in the transportation member in a locked position, and wherein in the configuration step the structural body is released from the locked position by rotating the structural body relative to the transportation member.

11. The method of treating inguinal hernia according to claim 1, wherein in the configuration step the structural member is caused to indwell in the position such that a distal portion of the structural member is disposed adjacent to a distal side of a gap in the fascia at the hernial site and an opposite proximal portion of the structural member is disposed adjacent to a proximal side of the gap in the fascia at the hernial site.

12. The method of treating inguinal hernia according to claim 11, wherein the structural member after being pushed out of the transportation member conforms to a shape of an inner wall of the bowel.

* * * * *